United States Patent

Rauleder et al.

[11] Patent Number: 6,142,024
[45] Date of Patent: Nov. 7, 2000

[54] APPARATUS AND METHOD FOR SAMPLING AND IR-SPECTROSCOPIC ANALYSIS OF HIGH-PURITY, HYGROSCOPIC LIQUIDS

[75] Inventors: Hartwig Rauleder; Klaus-Dieter Krieger; Lothar Zehe, all of Rheinfelden, Germany

[73] Assignee: Hüls Aktiengesellschaft, Marl, Germany

[21] Appl. No.: 09/177,657

[22] Filed: Oct. 23, 1998

[30] Foreign Application Priority Data

Oct. 23, 1997 [DE] Germany .......................... 197 46 862

[51] Int. Cl.[7] .............................. G01N 1/00; G01N 21/00
[52] U.S. Cl. .................................... 73/864.63; 73/863.71; 73/864.81; 250/428; 356/246
[58] Field of Search ........................... 73/864.63, 864.64, 73/864.81, 863.71; 356/244, 246; 250/428, 430

[56] References Cited

U.S. PATENT DOCUMENTS

| | | | |
|---|---|---|---|
| 3,769,505 | 10/1973 | Lee et al. ................................. | 250/430 |
| 3,932,040 | 1/1976 | Warncke ................................. | 356/246 |
| 4,038,055 | 7/1977 | Varano et al. . | |
| 4,363,972 | 12/1982 | Kuhlman et al. ........................ | 250/430 |
| 4,587,835 | 5/1986 | Adams . | |
| 4,588,893 | 5/1986 | Vidrine et al. ........................... | 250/428 |
| 4,668,091 | 5/1987 | Lagesson et al. ........................ | 356/246 |
| 4,692,621 | 9/1987 | Passaro et al. . | |
| 4,822,166 | 4/1989 | Rossiter ................................... | 356/246 |
| 5,220,401 | 6/1993 | Milosevic et al. ....................... | 356/246 |

FOREIGN PATENT DOCUMENTS

| | | |
|---|---|---|
| 0 414 446 | 2/1991 | European Pat. Off. . |
| 196 31 689 | 2/1997 | Germany . |
| WO 97/14029 | 4/1997 | WIPO . |

OTHER PUBLICATIONS

D.L. Wood, J.P. Luongo and S.S. DeBaia, Stainless Steel Cell for Infrared Spectrometric Analysis of Silicon and Germanium Halides, Analytical Chemistry, vol. 53, No. 12, Oct. 1981.

Thomas Y. Kometani, Darwin L. Wood and Joseph P. Luongo, Infrared Spectrophotometric Determination of Hydrogen–Containing Impurities in Silicon Tetrachloride, Analytical Chemistry, vol. 59, No. 8, Apr. 15, 1987.

*Primary Examiner*—Daniel S. Larkin
*Attorney, Agent, or Firm*—Oblon, Spivak, McClelland, Maier & Neustadt, P.C.

[57] ABSTRACT

An apparatus and method for the sampling and quantitative, IR-spectroscopic determination of impurities in hygroscopic liquids. The apparatus includes a stainless steel tube having a straight bore, a first end, and a second end. A first flange attachment is located at the first end of the stainless steel tube, and a second flange attachment is located at the second end of the stainless steel tube. First and second calcium fluoride plates are also located at the first and second ends of the steel tube, respectively. The first and second plates are oriented parallel to each other and perpendicular to the axis of the stainless steel tube. First and second outer flanges hold respective of the first and second plates in place at the first and second ends of the tube, respectively, and the first and second outer flanges are mechanically fixed to the first and second flange attachments, respectively. At least one seal separates the first plate from the first flange attachment and the first outer flange. Similarly, at least one seal separates the second plate from the second flange attachment and the second outer flange. First and second three-way taps are coupled by a first stainless steel line. A second stainless steel line couples the first three-way tap to the stainless steel tube, and a third stainless steel line couples the second three-way tap to the stainless steel tube. The method includes the steps of purging the first line with nitrogen gas and purging a cell space defined by the tube at least five times.

25 Claims, 5 Drawing Sheets

APPARATUS AND METHOD FOR SAMPLING AND IR-SPECTROSCOPIC ANALYSIS OF HIGH-PURITY, HYGROSCOPIC LIQUIDS

BACKGROUND OF THE INVENTION

1. Field of the Invention:

The present invention relates to an apparatus and method for sampling and analyzing impurities in hygroscopic liquids having a purity of more than 99.95% by weight. The present invention also relates to an apparatus and method for the quantitative, infra red spectroscopic (IR-spectroscopic) determination of impurities in hygroscopic liquids having a purity of more than 99.95% by weight.

2. Discussion of the Background:

High-purity products such as silicon tetrachloride are presently used, inter alia, in the production of optical fibers. The analytical methods employed in the quality control of high-purity liquids should correctly reflect the actual purity of the product. Particularly during sampling, additional impurities (e.g., moisture) might be introduced which may cause secondary reactions.

Conventionally, the impurities in silicon tetrachloride are determined quantitatively by IR spectroscopy. This process is described, for example, in Anal. Chem. 1987, 59, 1089–1093 and Anal. Chem. 1981, 53, 1967–1968.

Also, it is known that TEFLON-coated cells or cells made of stainless steel together with AgCl windows can be used for sampling and analysis in laboratories. However, in practice, undesired impurities might be introduced before the actual measurement when using the known methods and cells on an industrial scale.

SUMMARY OF THE INVENTION

Accordingly, an object of the present invention is to provide an apparatus and method for sampling and analyzing impurities in hygroscopic liquids on an industrial scale.

This and other objects of the present invention are achieved by providing an apparatus having a straight bore, a first end, and a second end. First and second flange attachments are located at respective of said ends. First and second plates made of calcium fluoride are also located at the first and second ends, respectively. The first and second plates are oriented parallel to each other and perpendicular to the axis of the stainless steel tube. First and second outer flanges hold respective of the first and second plates in place at the first and second ends of the tube, respectively. Said first and second outer flanges are mechanically fixed to the first and second flange attachments, respectively. At least one first seal separates the first plate from the first flange attachment and the first outer flange, and at least one second seal separates the second plate from the second flange attachment and the second outer flange. First and second three-way taps couple the first and second three-way taps. A second stainless steel line couples the first three-way tap to the stainless steel tube, and a third stainless steel line couples the second three-way tap to the stainless steel tube.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
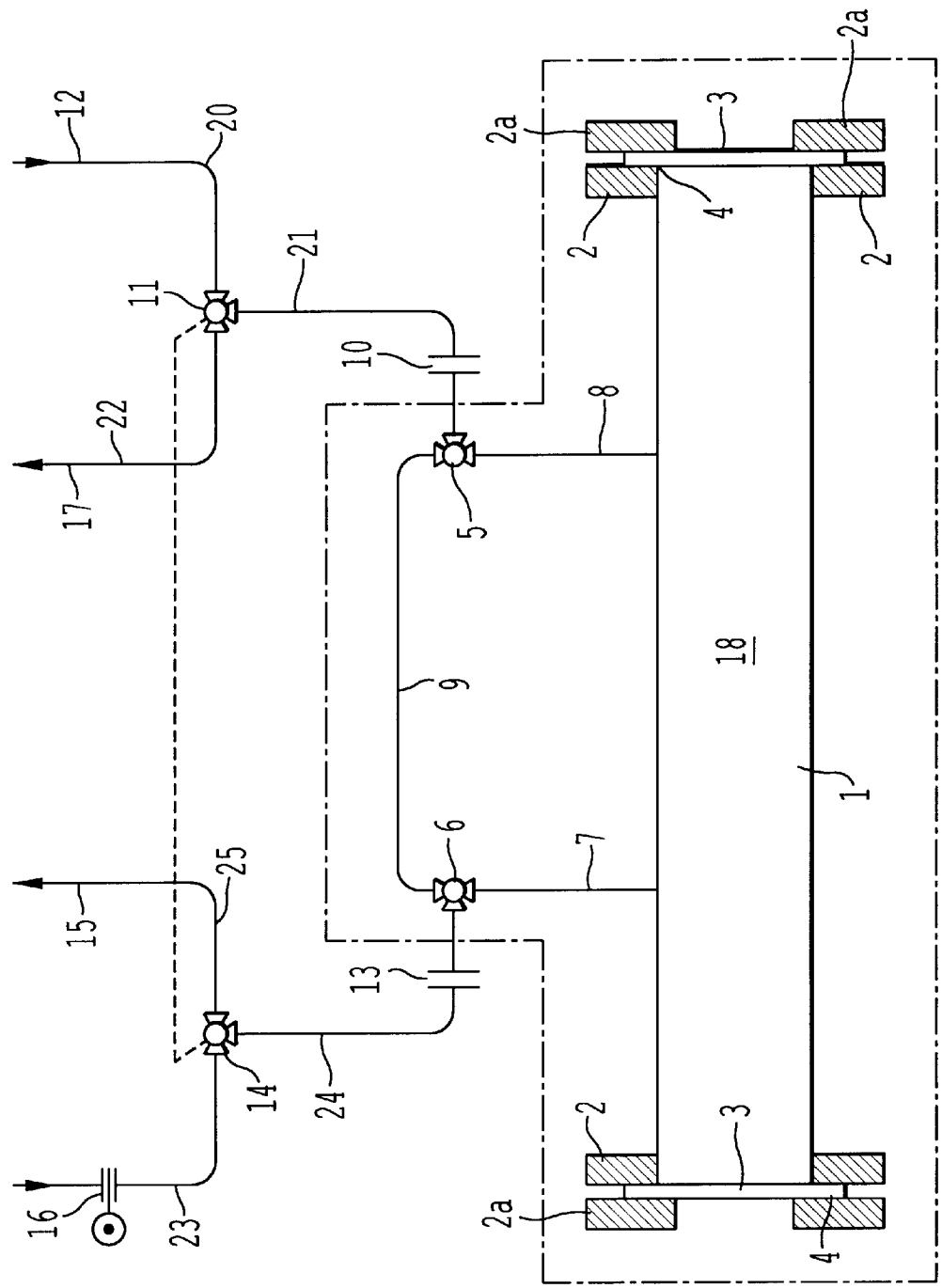
FIG. 1 is schematic illustration of an apparatus for the sampling and quantitative, IR-spectroscopic determination of impurities in hygroscopic liquids.

Referring now to the drawings, wherein like reference numerals designate identical or corresponding parts throughout the several views, and more particularly to FIG. 1 thereof, an apparatus suitable for reliable sampling and dependable, quantitative, IR-spectroscopic determination of impurities in hygroscopic liquids is shown. In particular, the apparatus is suitable for sampling and analyzing hygroscopic liquids having a purity of more than 99.95% by weight, and more particularly, high-purity silicon tetrachloride. A stainless steel tube 1 having a straight bore is provided. Flange attachments 2 are located at each end of the stainless steel tube 1. Together, the flange attachments 2 and the stainless steel tube 1 define a volume or cell space 18. Each of the flange attachments 2 includes a plate 3 made of calcium fluoride. The plates 3 are oriented parallel to each other and perpendicular to the axis of the stainless steel tube 1. The outer edges of each plate 3 are located between a portion of the corresponding flange attachment 2 and an annular outer flange 2a. The outer flanges 2a are mechanically fixed to the corresponding portions of the flange attachments 2 so that the plates 3 are held in place. At least one seal 4 is provided between each of the parallel plates 3 and the corresponding flange attachment 2 and flange 2a. A first three-way tap 5 is connected to a second three-way tap 6 via a stainless steel line 9. A first stainless steel line 8 connects the first tap 5 to the stainless steel tube 1, and a second stainless steel line 7 connects the second tap 6 to the stainless steel tube 1. The first tap 5 is connected to a first connection point 10, and the second tap 6 is connected to a second connection point 13.

A supply line 20 connects a dry nitrogen supply 12 to a third three-way tap 11. A supply line 21 connects the third tap 11 to the connection point 10. A supply line 23 connects a plant section 16 to a fourth three-way tap 14. A supply line 24 connects the fourth tap to the connection point 13. High-purity liquid to be analyzed is taken from the plant section 16. A line 22 connects an outlet 17 to the tap 11, and a line 25 connects an outlet 15 to a tap 14.

Preferably, the stainless steel tube 1 has an internal diameter of from 1 to 3 cm and an internal length of from 5 to 20 cm. Preferably, the volume of the cell space 18 (also called the cell volume) is from 5 to 140 $cm^3$, and most preferably from 10 to 100 $cm^3$. All stainless steel parts (including the tube 1 and the lines 7, 8, and 20–25) are constructed of corrosion resistant steel, for example VA steels.

The plates 3 preferably have a thickness of from 2 to 10 mm and a diameter of from 15 to 50 mm. The seals 4 are preferably constructed of a fluorinated polymer, for example, Viton or Kalrez seals.

Figure 4:
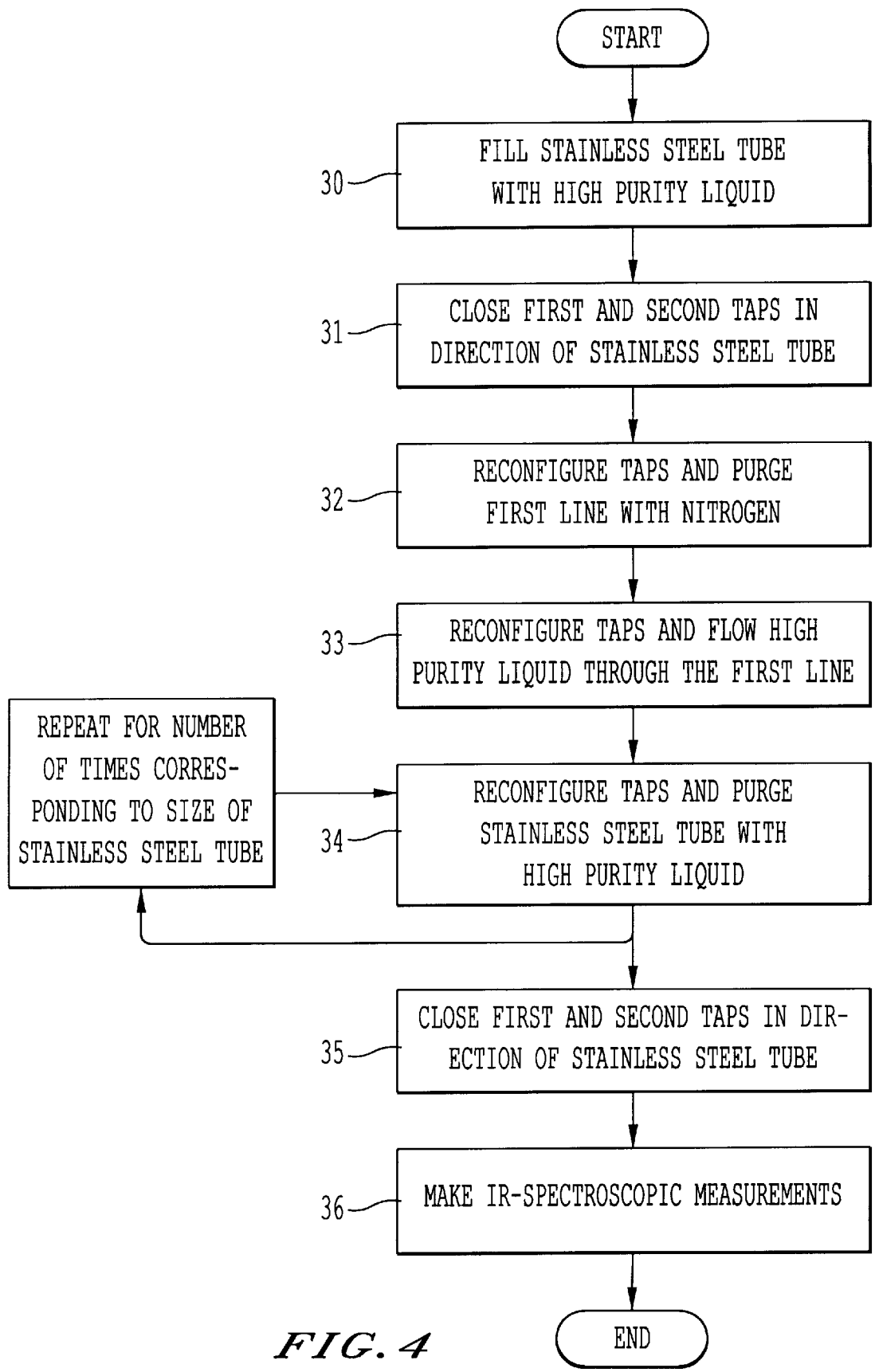
FIG. 4 is a flow chart describing a first way of performing the inventive method.

FIG. 4 is a flow chart describing a method for the sampling and the quantitative, IR-spectroscopic determination of impurities in hygroscopic liquids, particularly high-purity silicon tetrachloride having a purity of more than 99.95% by weight. The method of FIG. 4 may be performed using the apparatus described in FIG. 1.

In step 30, the stainless steel tube is filled with a high-purity liquid, preferably high-purity silicon tetrachloride. Then in step 31, the first and second taps 5 and 6 are closed in the direction of lines 7 and 8, respectively.

Between 1 and 24 hours after step 31, a nitrogen purge is performed by flowing nitrogen gas from the nitrogen gas source 12 in step 32. Also in step 32, the first, second, third, and fourth taps 5, 6, 11, and 14 are adjusted so that the nitrogen gas flows from the nitrogen gas source 12 to an outlet 15 via the line 20, the line 21, the connection point 10, the line 9, the connection point 13, the line 24, and the line 25. The nitrogen purge preferably lasts between 0.1 to 12 hours Then, in step 33 taps 11 and 14 are readjusted so that high purity liquid, preferably high-purity silicon tetrachloride, flows from the plant section 16 to the outlet 17 via the line 23, the line 24, the connection point 13, the line 9, the connection point 10, the line 21, and the line 22.

Next, in step 34 the stainless steel tube 1 is purged with the high purity liquid by adjusting the taps 14, 6, and 5 so that the high purity liquid flows from the plant section 16 to the stainless steel tube via the line 23, the line 24, the connection point 13, and the line 7. The stainless steel tube 1 is purged (filled and emptied) for a number of times corresponding to the volume of the cell space 18, preferably five times, most preferably between 10 and 30 times.

In step 35, the taps 5 and 6 are closed in the direction of the lines 8 and 7, respectively, and then, in step 36 IR-spectroscopic measurements are performed in a known manner.

Figure 5:
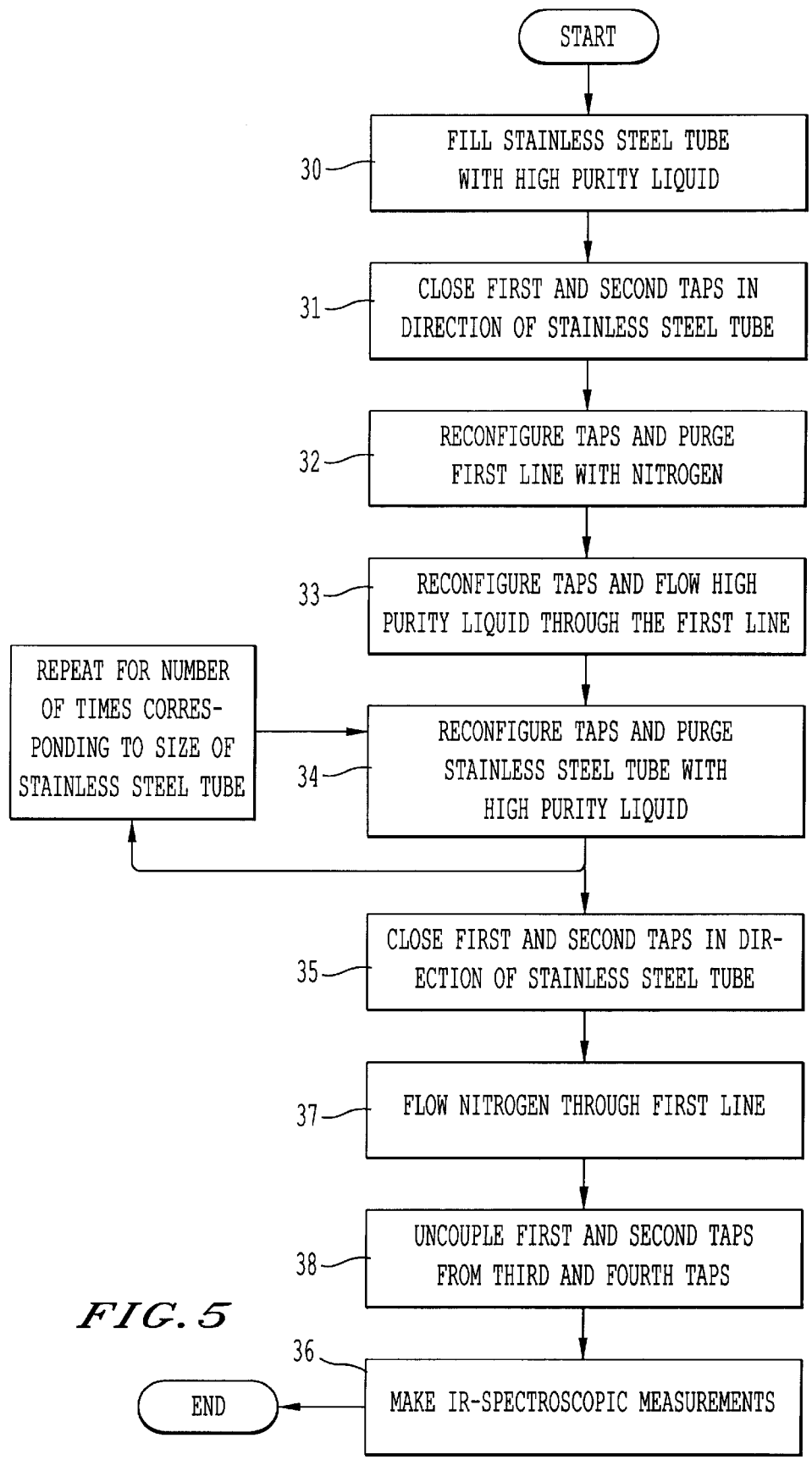
FIG. 5 is a flow chart describing a second way of performing the inventive method.

Within industrial plants, the method of the invention can advantageously be carried out "on the spot." However, as shown in FIG. 5, it is also possible, after carrying out step 34, to close the taps 5 and 6 in the direction of the lines 7 and 8 in step 35, and adjust taps 11 and 14 so that dry nitrogen flows though the line 9 in the direction of the outlet 15 in step 37. Next, in step 38 the connection points 13 and 10 are disconnected, and then, in step 35 IR-spectroscopic measurements are taken.

The apparatus and method of the present invention permits reliable quality control measurements to be performed on high-purity liquids, in particular silicon tetrachloride—even in industrial plants.

The present invention is illustrated by way of the following example without the scope of the invention being limited thereby.

EXAMPLE

Figure 2:
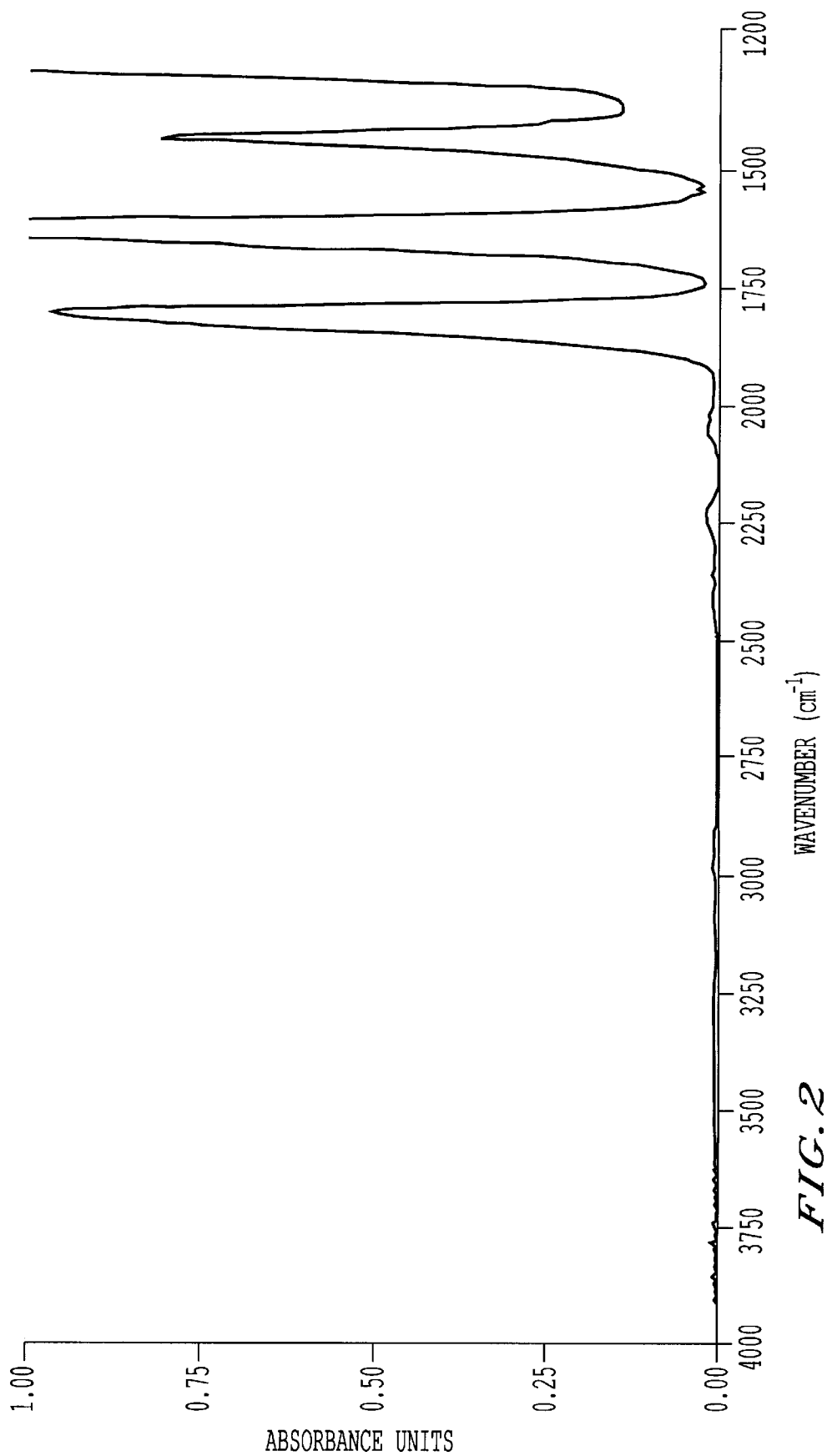
FIG. 2 is a graph showing the relationship between absorbance units and wave number based on the results of IR-spectroscopic analysis performed in accordance with the invention.

For carrying out the sampling and the IR-spectroscopic analysis under conditions according to the invention, the apparatus shown in FIG. 1 was assembled, filled with the product (high-purity silicon tetrachloride) and allowed to stand for a number of hours. The sample material to be analyzed was then passed through the cell so as to displace the cell contents. The cell volume of material in the cell was replaced at least five times. Finally, the cell was introduced into the sample space of a commercial infra-red spectrometer and measured in the range from 4,000 to 1,200 $cm^{-1}$ at a resolution of 2 $cm^{-1}$. As shown in FIG. 2, only harmonic vibrations of silicon tetrachloride were observed in the spectrum. Virtually no bands of secondary components were detected.

Comparative Example

To record the IR spectrum under standard sampling conditions, a new glass bottle which had been rinsed beforehand with product was filled with sample material to be analyzed from the same product as above. Using a glass syringe which had likewise been rinsed beforehand with product, the sample was taken from the bottle and introduced into a cell. The cell was formed by a cylindrical glass body with lateral ports and ground glass joints. Stoppers and calcium fluoride windows were placed at the ends of the two tube openings. After the filling procedure, the cell was measured with the same infra-red spectrometer as used in the Example above.

Figure 3:
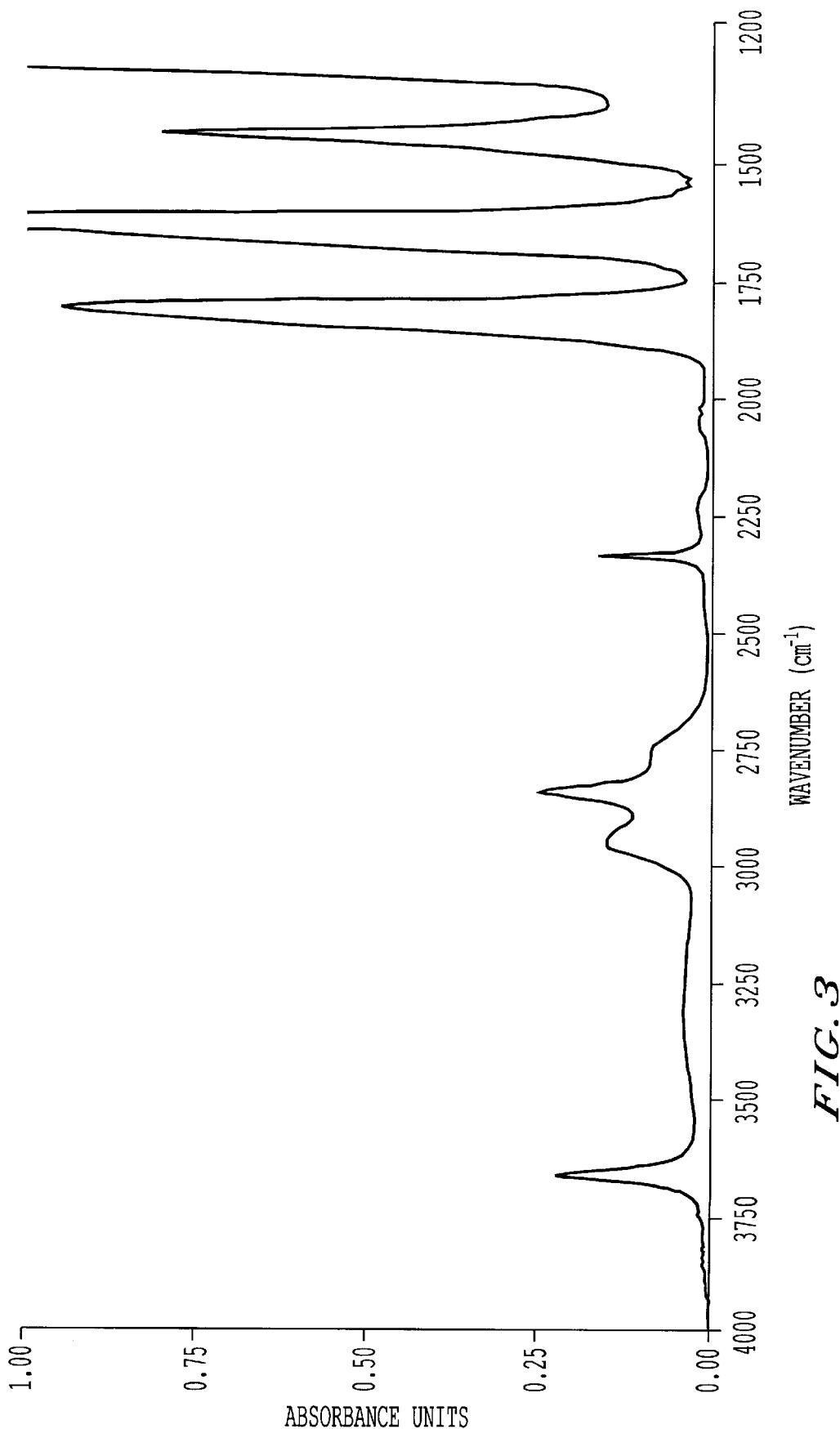
FIG. 3 is a graph showing the relationship between absorbance units and wave number based on the results of IR-spectroscopic analysis performed under conventional conditions.

As shown in FIG. 3, apart from the harmonic vibrations, the following additional bands occur: a band in the region of 3,670 $cm^{-1}$ (the SiOH band); a band in the range from 2,600 to 3,100 $cm^{-1}$ (the HCl bands); and a band in the region of 2,350 $cm^{-1}$ (the $CO_2$ band). These bands are believed to have been caused, inter alia, by the handling of the sample. Thus, the apparatus and method of the present invention are believed to eliminate the additional bands.

Obviously, numerous modifications and variations of the present invention are possible in light of the above teachings. It is therefore to be understood that within the scope of the appended claims, the invention may be practiced otherwise than as specifically described herein.

What is claimed is:

1. An apparatus for the sampling and the quantitative, infra red spectroscopic determination of impurities in hygroscopic liquids, comprising:

a stainless steel tube having a straight bore, a first end, and a second end;

first flange attachment located at the first end and a second flange attachment located at the second end;

a first calcium fluoride plate and a second calcium fluoride plate located at respective of said first end and said second end, said first and second calcium fluoride plates being oriented parallel to each other and perpendicular to the axis of the stainless steel tube;

first and second outer flanges holding respective of the first and second calcium fluoride plates in place at the first and second ends of the tube, respectively, said first and second outer flanges being mechanically fixed to the first and second flange attachments, respectively;

an at least one first seal separating the first plate from the first flange attachment and the first outer flange;

an at least one second seal separating the second plate from the second flange attachment and the second outer flange;

first and second three-way taps;

a first stainless steel line coupling the first and second three-way taps;

a second stainless steel line coupling the first three-way tap to the stainless steel tube; and a third stainless steel line coupling the second three-way tap to the stainless steel tube.

2. An apparatus as claimed in claim 1, wherein the stainless steel tube has an internal diameter of from 1 to 3 centimeters, an internal length of from 5 to 20 centimeters, and a cell volume of from 5 to 140 cubic centimeters.

3. An apparatus as claimed in claim 2, wherein the first and second seals comprise a fluorinated polymer.

4. An apparatus as claimed in claim 2, wherein the calcium fluoride plate has a thickness of from 2 to 10 millimeters and a diameter of from 15 to 50 millimeters.

5. An apparatus as claimed in claim 1, wherein the first and second seals comprise a fluorinated polymer.

6. An apparatus as claimed in claim 5, wherein the calcium fluoride plate has a thickness of from 2 to 10 millimeters and a diameter of from 15 to 50 millimeters.

7. An apparatus as claimed in claim 1, wherein the calcium fluoride plate has a thickness of from 2 to 10 millimeters and a diameter of from 15 to 50 millimeters.

8. A method for preparing a high purity liquid for infra red analysis, comprising:

filling a stainless steel tube of an apparatus with a high-purity liquid, said stainless steel tube partially defining a cell space and having a straight bore, a first end, and a second end;

placing a first tap, a second tap, a third tap, and a fourth tap in a first configuration, said first tap being coupled to the stainless steel tube and to the second tap by a first line, said second tap being coupled to said stainless steel tube, said third tap being coupled to said first tap and a nitrogen source and a first outlet, said fourth tap being coupled to said second tap and a source for the high purity liquid and a second outlet;

purging the first line with nitrogen gas by flowing nitrogen gas from the nitrogen gas source to the second outlet;

reconfiguring the first, second, third, and fourth taps;

flowing the high-purity liquid through the first line by flowing the high-purity liquid from the high purity liquid source to the first outlet;

reconfiguring the first, second, and third taps;

purging the cell space with the high-purity liquid by flowing the high purity liquid from the high purity liquid source to the cell space; and performing an infra red spectroscopic measurement on a sample of the high purity liquid within the cell space.

9. The method as claimed in claim 8, wherein at least one hour elapses after said step of filling the stainless steel tube and before said step of purging the first line with nitrogen gas.

10. The method as claimed in claim 9, wherein the step of purging the first line with nitrogen gas lasts continuously for at least 0.1 hour.

11. The method as claimed in claim 10, wherein the step of purging the cell space is performed for a number of times based on the volume of the cell, said number being at least five.

12. The method as claimed in at least one of claim 11, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

13. The method as claimed in claim 10, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

14. The method as claimed in claim 9, wherein the step of purging the cell space is performed for a number of times based on the volume of the cell, said number being at least five.

15. The method as claimed in at least one of claim 14, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

16. The method as claimed in claim 9, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

17. The method as claimed in claim 8, wherein the step of purging the first line with nitrogen gas lasts continuously for at least 0.1 hour.

18. The method as claimed in claim 17, wherein the step of purging the cell space is performed for a number of times based on the volume of the cell, said number being at least five.

19. The method as claimed in at least one of claim 18, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

20. The method as claimed in claim 17, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

21. The method as claimed in claim 8, wherein the step of purging the cell space is performed for a number of times based on the volume of the cell, said number being at least five.

22. The method as claimed in claim 21, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

23. The method as claimed in claim 8, further comprising the steps of:

closing the first and second taps in the direction of the stainless steel tube after the step of purging the cell space;

flowing nitrogen gas from the nitrogen gas source to the second outlet; and uncoupling the first and second taps from the third and fourth taps, respectively, before the step of performing the infra red spectroscopic measurement.

24. The method of claim 8, wherein the high purity liquid is a hygroscopic liquids having a purity of more than 99.95% by weight.

25. The method of claim 24, wherein the high purity liquid is silicon tetrachloride having a purity of more than 99.95% by weight.

* * * * *